United States Patent [19]

Tomcufcik et al.

[11] 4,269,832

[45] May 26, 1981

[54] METHOD OF TREATING ARTHRITIC DISEASE

[75] Inventors: Andrew S. Tomcufcik, Old Tappan, N.J.; Adolph E. Sloboda, New City, N.Y.

[73] Assignee: American Cyanamid Company, Stamford, Conn.

[21] Appl. No.: 95,813

[22] Filed: Nov. 19, 1979

Related U.S. Application Data

[63] Continuation-in-part of Ser. No. 17,797, Mar. 5, 1979, abandoned, which is a continuation-in-part of Ser. No. 895,572, Apr. 12, 1978, abandoned.

[51] Int. Cl.$^3$ ............... A61U 27/00; A61U 31/33; A61U 31/53; A61U 31/54
[52] U.S. Cl. ............... 424/244; 424/246; 424/248.4; 424/249
[58] Field of Search ............... 544/196, 198, 113, 60; 260/243.3; 424/244, 249, 246, 248.4

[56] References Cited

U.S. PATENT DOCUMENTS

| | | | |
|---|---|---|---|
| 2,691,021 | 10/1954 | Kaiser et al. | 544/196 |
| 3,265,690 | 8/1966 | Matter et al. | 544/113 |
| 3,591,693 | 7/1971 | Cantrall et al. | 424/249 |
| 3,706,741 | 12/1972 | Papaioannou | 544/196 |

FOREIGN PATENT DOCUMENTS 1013233  12/1965  United Kingdom ............... 544/196

*Primary Examiner*—Stanley J. Friedman
*Attorney, Agent, or Firm*—Edward A. Conroy, Jr

[57] ABSTRACT

This disclosure describes compositions of matter useful as anti-inflammatory agents and as inhibitors of the progressive joint deterioration characteristic of arthritic disease and the methods of meliorating inflammation and of inhibiting joint deterioration in mammals therewith, the active ingredients of said compositions of matter being certain 2-(substituted-amino)-4,6-bis(alkylamino)-s-triazines.

3 Claims, No Drawings

METHOD OF TREATING ARTHRITIC DISEASE

CROSS REFERENCE TO RELATED APPLICATION

This application is a continuation-in-part of our copending application Ser. No. 17,797, now abandoned, filed Mar. 5, 1979, which is a continuation-in-part of our abandoned application Ser. No. 895,572, filed Apr. 12, 1978.

BRIEF SUMMARY OF THE INVENTION

This invention relates to novel compositions of matter useful as anti-inflammatory agents and as inhibitors of the progressive joint deterioration characteristic of arthritic disease. More particularly, it relates to therapeutic compositions containing certain $N_2$-substituted-$N_4,N_6$-bis(alkyl)melamines which meliorate inflammation and inhibit arthritic joint deterioration in mammals. The invention includes the new compositions of matter and the methods of meliorating inflammation and of inhibiting joint deterioration in mammals therewith. The active ingredients of the novel compositions of this invention may be represented by the following structural formula:

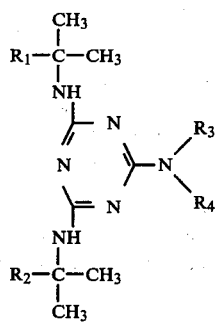

wherein $R_1$ and $R_2$ are each individually selected from the group consisting of methyl, tert.-butyl, tert.-amyl, neopentyl and 3,3-dimethylbutyl; $R_3$ is hydrogen or alkyl having up to 4 carbon atoms; $R_4$ is tert.-butyl,1,1,2,2-tetramethylpropyl, 1,1,2,2-tetramethylbutyl, 1,1,3,3-tetramethylbutyl, 1,1,4,4-tetramethylamyl, 2-(2-pyridyl)ethyl or a monovalent moiety of the formula:

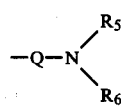

wherein Q is a divalent moiety selected from the group consisting of those of the formulae:

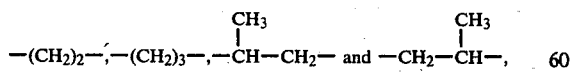

$R_5$ is alkyl having up to 4 carbon atoms, $R_6$ is alkyl having up to 4 carbon atoms, and $R_5$ and $R_6$ taken together with their associated N(itrogen) is piperidino, morpholino, pyrrolidino or thiomorpholino; and $R_3$ and $R_4$ taken together with their associated N(itrogen) is pyrrolidino, piperidino, hexamethyleneimino, heptamethyleneimino or a monovalent moiety of the formula:

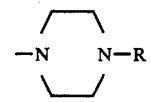

wherein R is hydrogen, alkyl having up to 4 carbon atoms, phenyl, p-methoxyphenyl or carboalkoxy having up to 4 carbon atoms.

DETAILED DESCRIPTION OF THE INVENTION

The active compounds of the present invention are obtainable as crystalline materials having characteristic melting points and absorption spectra. They are appreciably soluble in many organic solvents such as lower alkanols, acetone, ethyl acetate, and the like, but are generally insoluble in water. These compounds are capable of forming acid-addition and quaternary ammonium salts with a variety of organic and inorganic salt-forming reagents when the substituent $-NR_3R_4$ contains a basic nitrogen atom. Thus, acid-addition salts, formed by admixture of the organic free base with an equivalent of an acid, suitably in a neutral solvent, are formed with such acids as sulfuric, phosphoric, hydrochloric, hydrobromic, citric, tartaric, acetic, and related acids. In like manner, quaternary ammonium salts may be formed by reaction of the free bases with an equivalent of a variety of organic esters of sulfuric, hydrohalic and aromatic sulfonic acids. The organic reagents employed for quaternary ammonium salt formation are preferably lower alkyl halides. The acid-addition and quaternary ammonium salts of the active compounds of the present invention are, in general, crystalline solids relatively soluble in water, methanol and ethanol but relatively insoluble in non-polar organic solvents such as diethyl ether, benzene, toluene, and the like. For purposes of this invention, the free bases are equivalent to their non-toxic acid-addition and quaternary ammonium salts.

The $N^2$-substituted-$N^4,N^6$-bis(alkyl)melamines of the novel compositions of the present invention may be readily prepared from cyanuric chloride (I) as set forth in the following reaction scheme:

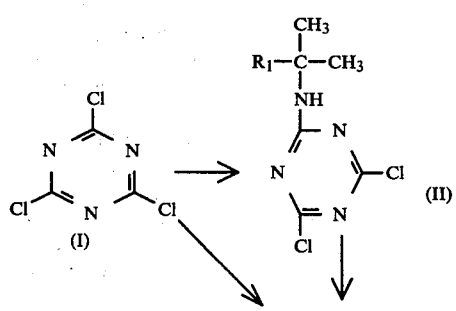

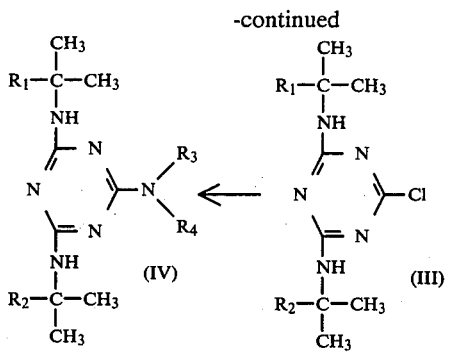

-continued wherein $R_1$, $R_2$, $R_3$ and $R_4$ are as hereinabove defined. In accordance with the above reaction scheme, cyanuric chloride (I) is reacted with one molecular equivalent of an amine of the formula $R_1$—$C(CH_3)_2$—$NH_2$ to provide the corresponding 2-(alkylamino)-4,6-dichloro-s-triazine (II). Treatment of (II) with one molecular equivalent of an amine of the formula $R_2$—$C(CH_3)_2$—$NH$ then provides the corresponding 2-chloro-4,6-bis(alkylamino)-s-triazine (III). Treatment of the latter intermediate with an amine of the formula:

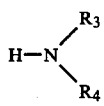

wherein $R_3$ and $R_4$ are as hereinabove defined then provides the active compounds (IV) of the present invention. The above reactions may be carried out in an inert solvent such as toluene or xylene for a period of time of from about 3 hours to 24 hours or more at temperatures ranging from about 25° C. to about 200° C. In addition, α-pyridone may be employed as catalyst in solvents or as a reaction medium. Variation in the reaction time and temperature is dependent upon the structure of the alkylamine reagents; and an acid scavenger such as sodium bicarbonate, soda ash, or a tertiary amine such as diisopropylethylamine should be employed to take up the hydrochloric acid produced in the reaction. In those cases where an excess of alkylamine may be used, then an acid scavenger and/or an inert solvent may be dispensed with. Where $R_1$ and $R_2$ are the same, then treatment of (I) with two molecular equivalents of amine provides the intermediate (III) directly.

The active compounds of the present invention have been found to be highly useful for meliorating inflammation and associated joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gm. to about 7.0 gm. of the active ingredient for a subject of about 70 kg. of body weight are administered in a 24 hour period. This dosage regimen may be adjusted to provide the optimum therapeutic response. For example, several divided dosses may be administered daily or the dose may be proportionally reduced as indicated by the exigencies of the therapeutic situation. A decided practical advantage of this invention is that the active ingredient may be administered in any convenient manner such as by the oral, intravenous, intramuscular, topical, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg./ml. of the finished compositions. These active compounds are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

Adjuvant-induced experimental polyarthritis is a specific systemic disease of the rat which shares interesting similarities with rheumatoid arthritis. Specifically, the histology of the two diseases bears a remarkable resemblance as shown by C. M. Pearson et al., Am. J. Pathol. 42, 73 (1963). E. M. Glenn, Am. J. Vet. Res. 27 (116), 339 (1966) has classified adjuvant-induced polyarthritis as a crippling and permanent deformity resulting from diffuse connective tissue involvement around certain susceptible joints in the rat. Zahiri et al., Can. Med. Ass. J. 101, 269 (1969) have shown that the fusiform swelling of the distal joints is associated with edema, congestion and synovitis including pannus formation, all of which precede the ultimate destruction of bone and cartilage. Furthermore, Zahiri et al. indicate that the cartilage destruction in the joint is due to an invasive pannus which originates in the marginal synovium and extends across the articular surface to erode it. When non-steroidal, anti-inflammatory agents such as indomethacin inhibit arthritic paw swelling, which is composed of inflammatory cell infiltrates, they have also been shown to prevent joint and bone deterioration. See S. Wong et al., J. Pharm. & Exptl. Ther. 185, 127 (1973) and G. R. Bobalick et al., Agents & Actions 4, 364 (1974). The most pertinent reference showing the relationship between arthritis and joint deterioration is an X-ray analysis of adjuvant arthritis in the rat by Blackham et al., Agents & Actions 7, 145 (1977). In a similar manner, inhibition of the progress of arthritis in paws of rats treated with the compounds of this invention also lessens associated joint deterioration.

The following test shows the activity of the compounds of this invention against chronic inflammation in adjuvant-induced arthritis which is accompanied by joint destruction. Groups of three Royal Hart, Wistar strain rats weighing 200±10 grams each were injected intradermally in the right hind paw with Freund's adjuvant (dried human tubercle bacilli in a mineral oil vehicle) at a dose of 2 mg./kg. of body weight. Test compounds were administered orally in a 1.5% starch vehicle at various doses once daily on days 0 through 13 post challenge. Control rats were treated in a similar manner, but given only starch vehicle. On the 14th and 21st day post challenge the diameter of the injected paw (primary lesion) was measured by micrometer caliper. The volume of inflamed paws were estimated from these measurements and the results are expressed as percent inhibition of swelling as compared to controls. At the same time, the other inflamed sites, such as ears, paws and tail (secondary lesions) were observed and each rat was graded as to degree of inflammation and swelling present. The grading is based on a scale of 0 to 24 where 0 represents a complete absence of induced arthritic nodules and 24 represents the maximum degree of inflammation. The mean grade for each treated group is calculated and the effects of each compound are expressed as percent inhibition of the control grade. Table I below records the results of tests conducted with the active compounds of this invention and known anti-inflammatory agents. The active compounds of this invention appear to suppress the progression of the arthritis and associated joint deterioration.

TABLE I

| | The Effect of Anti-Inflammatory Agents on Adjuvant Arthritis In Rats | | | | | | | |
|---|---|---|---|---|---|---|---|---|
| | Oral Dose mg./kg. of | Dead/Treated | Mean Weight Gain (grams) | | % Inhibition of Swelling (primary lesion) | | % Inhibition of Control Grade (secondary lesion) | |
| Compound | Body Wgt. | at 21 Days | Day 14 | Day 21 | Day 14 | Day 21 | Day 14 | Day 21 |
| Normal rats | — | 8/186 | 77 | 112 | — | — | — | — |
| Adjuvant Controls | — | 56/630 | 36 | 31 | 0 | 0 | 0 | 0 |
| $N^2$, $N^4$, $N^6$-Tris(1,1,2,2-tetramethylpropyl)melamine | 50 | 2/18 | 60 | 55 | 51 | 31 | — | — |
| $N^2$-(2-Morpholinoethyl)-$N^4$,$N^6$-bis(1,1,2,2-tetramethylpropyl)melamine dihydrochloride | 50 | 4/18 | 44 | 59 | 32 | 26 | — | — |
| 2-[4-(p-Methoxyphenyl)-1-piperazinyl]-4,6-bis-[1,1,2,2-tetramethylpropyl)amino]-s-triazine | 50 | 1/18 | 56 | 47 | 38 | 15 | — | — |
| $N^2$-(2-Diethylaminoethyl)-N-$^2$-ethyl-$N^4$,$N^6$-bis(1,1,2,2-tetramethylpropyl)melamine dihydrochloride | 50 | 11/18 | 47 | 65 | 58 | 31 | — | — |
| 4-{4,6-Bis[(1,1,2,2-tetramethylpropyl)-amino]-s-triazin-2-yl}-1-piperazinecarboxylic acid ethyl ester | 100 | 2/18 | 61 | 62 | 41 | 15 | 53 | 16 |
| | 50 | 7/36 | 58 | 59 | 40 | 24 | 39 | 19 |
| | 25 | 2/18 | 69 | 60 | 40 | 9 | 34 | 10 |
| $N^2$-Methyl-$N^2$-[2-(2-pyridyl)ethyl]-$N^4$,$N^6$-bis(1,1,2,2-tetramethylpropyl)melamine | 50 | 4/21 | 34 | 56 | 41 | 30 | — | — |
| $N^2$-(2-Dimethylamino- | | | | | | | | |

TABLE I-continued

The Effect of Anti-Inflammatory Agents on Adjuvant Arthritis In Rats

| Compound | Oral Dose mg./kg. of Body Wgt. | Dead/Treated at 21 Days | Mean Weight Gain (grams) | | % Inhibition of Swelling (primary lesion) | | % Inhibition of Control Grade (secondary lesion) | |
|---|---|---|---|---|---|---|---|---|
| | | | Day 14 | Day 21 | Day 14 | Day 21 | Day 14 | Day 21 |
| ethyl)-$N^2$-methyl-$N^4$,$N^6$-bis(1,1,2,2-tetramethylpropyl)melamine dihydrochloride | 50 | 6/15 | 29 | 59 | 70 | 50 | — | — |
| $N^2$-(2-Dimethylamino-1-methylethyl)-$4^4$,$N^6$-bis-(1,1,2,2-tetramethylpropyl)melamine dihydrochloride | 50 | 7/18 | 38 | 53 | 65 | 42 | — | — |
| 2-(1-Piperazinyl)-4,6-bis[(1,1,2,2-tetramethylpropyl)amino]-s-triazine | 50 | 4/18 | 34 | 73 | 58 | 38 | — | — |
| Indomethacin | 2 | 8/57 | 68 | 68 | 51 | 24 | 38 | 25 |
| | 1 | 9/54 | 63 | 65 | 46 | 19 | 34 | 20 |
| | 0.5 | 5/54 | 53 | 51 | 40 | 20 | 25 | 17 |
| | 0.25 | 0/9 | 51 | 57 | 30 | 4 | 22 | 4 |
| Aspirin | 400 | 18/57 | 41 | 55 | 73 | 48 | 58 | 45 |
| | 200 | 10/66 | 40 | 44 | 48 | 27 | 26 | 17 |
| | 100 | 18/63 | 48 | 53 | 36 | 13 | 19 | 8 |
| | 50 | 2/21 | 56 | 44 | 23 | 3 | 12 | 9 |
| Phenylbutazone | 150 | 2/27 | 40 | 50 | 75 | 44 | 54 | 31 |
| | 75 | 2/39 | 51 | 50 | 62 | 28 | 27 | 15 |
| | 37.5 | 5/39 | 53 | 53 | 56 | 14 | 18 | 13 |
| | 18.8 | 2/21 | 50 | 45 | 31 | 7 | 4 | 8 |

The invention will be described in greater detail in conjunction with the following specific examples.

EXAMPLE 1

Preparation of $N^2$,$N^4$,$N^6$-tris(1,1,3,3-tetramethylbutyl)melamine

A mixture of 3.7 g. (0.01 mole) of 2,4-bis(2,4,4-trimethyl-2-pentylamino)-6-chloro-s-triazine, 2.6 g. (0.02 mole) of 2,4,4-trimethyl-2-pentylamine and 2.85 g. (0.03 mole) of α-pyridone are fused and heated at the boiling point for 2½ hours during which time the mixture turns a brown color. At the end of this period the mixture is cooled yielding a solid mass which is treated with about 10 ml. of 10% sodium hydroxide. On filtration, 4.52 g. of a beige solid is obtained m.p. 151°–156° C. Recrystallization of the beige solid from 75 ml. of hot ethanol yields 3.09 g. of colorless needles, m.p. 156°–157.5° C.

EXAMPLE 2

Preparation of 2-chloro-4,6-bis(1,1,2,2-tetramethylpropylamino)-s-triazine 6.7 g. (0.044 mole) 2,3,3-trimethyl-2-butylamine hydrochloride and 3.4 g. (0.84 mole) NaOH in 20 ml. water are added to a stirred slurry of 3.6 g. (0.02 mole) cyanuric chloride in 150 ml. water. The reaction mixture is heated at reflux for 2½ hours, cooled and filtered to give the product, a white solid, m.p. 129°–131° C., 6.5 g.

EXAMPLE 3

Preparation of 2,4,6-tris(1,1,2,2-tetramethylpropylamino)-s-triazine 3.3 g. (9.6 mmole) of 2-chloro-4,6-di(2,3,3-trimethyl-2-butyl)amino-s-triazine and 3.3 g. (30 mmoles) of 2,3,3-trimethyl-2-butylamine are heated at reflux (oil bath 185° C.) for 21 hours. Thin layer chromatography of a sample of the reaction mixture indicates a mixture of starting material and product in a ratio of 3:7. Heating is terminated and the reaction mixture is treated with excess aqueous NaOH. Filtration affords a 4.9 g. of crude beige product. This is digested with 15 ml. of hot acetone, filtered and 2.6 g. of beige solid collected, m.p. 278° C. dec. Recrystallization of this product from hot ethanol gives the pure product, m.p. 317°–321° C. dec.

EXAMPLE 4

Preparation of 2,4-bis(1,1,3,3-tetramethylbutylamino)-6-chloro-s-triazine 18.4 g. (0.10 mole) of cyanuric chloride is slurried in 100 ml. of water and the suspension cooled in an ice bath. Two drops of phenolphthalein solution are added, followed by addition of 32.3 g. (0.25 mole) 2,4,4-trimethyl-2-pentylamino whereupon an exothermic reaction ensues. The suspension is heated with stirring at reflux for a total of 17 hours. During the first half hour a solution of 8.0 g. (0.20 mole) sodium hydroxide in 40 ml. of water is added slowly so as to keep the reaction mixture slightly alkaline. The reaction mixture is cooled, and the aqueous solution decanted from the waxy solid. Acetone is added to the solid and the mixture is filtered to give 33.3 g. of product, m.p. 164°–168° C. Recrystallization from hot ethanol gives 27.5 g. of white needles, m.p. 165°–167° C.

EXAMPLE 5

$N^2$-(2-Morpholinoethyl)-$N^4$,$N^6$-bis(1,1,2,2-tetramethylpropyl)melamine dihydrochloride A 785 g. portion of 2,3,3-trimethylbutene and 408 g. of 96% sodium cyanide are placed in a 22 liter flask and chilled to 10° C. One liter of glacial acetic acid at 10° to 15° C. is added over a period of 20 minutes and then a solution of 2 kg. of concentrated sulfuric acid in one liter of glacial acetic acid is added over a period of 2 hours at 25°–30° C. The mixture is stirred for 4 hours and allowed to stand at room temperature. A solution of 4.7 kg. of sodium hydroxide in 9.8 liters of water is added over a period of 1.5 hours, keeping the temperature below 50° C. The reaction mixture is then heated at 95°-100° C. for 4 hours and allowed to cool with stirring overnight. The liquid portion of the mixture is extracted with ether. The residual salt is diluted with 4 liters of water, stirred for ½ hour and extracted with ether. The combined ether extracts are dried over magnesium sulfate, filtered through charcoal, allowed to stand at room temperature, chilled and saturated with hydrogen chloride gas. The solid is collected, washed with ether and dried giving 1208 g. of 2,3,3-trimethyl-2-butylamine hydrochloride.

A 50 g. portion of the above product and 27.6 g. of cyanuric chloride are suspended in 750 ml. of water with stirring. A solution of 25.5 g. of sodium hydroxide in 150 ml. of water is added and the mixture is stirred and heated at reflux for 3 hours. The mixture is chilled in an ice bath and then filtered, giving a solid which is broken up, suspended in boiling water, allowed to cool, stored in a chill room overnight, filtered and dried giving 43 g. of 2-chloro-4,6-bis[(1,1,2,2-tetramethylpropyl)amino]-s-triazine.

A mixture of 8.56 g. of the above product and 13 g. of morpholinoethylamine is heated at 140°-150° C. for 2 hours. The reaction mixture is poured into 200 ml. of water giving a colorless solid which is collected and dissolved in 150 ml. of ether. The ether solution is dried over magnesium sulfate, filtered and the filtrate is treated with excess hydrochloric acid in isopropanol giving a colorless crystalline solid. This solid is collected, washed with ether, dried and dissolved in 500 ml. of boiling ethanol. The solution is treated with charcoal, filtered, and cooled, giving the desired product as a colorless solid, mp. 270°-275° C.

EXAMPLE 6

2-[4-(p-Methoxyphenyl)-1-piperazinyl]-4,6-bis[(1,1,2,2-tetramethylpropyl)amino]-s-triazine A mixture of 6.84 g. of 2-chloro-4,6-bis[(1,1,2,2-tetramethylpropyl)amino]-s-triazine and 7.69 g. of N-(p-methoxyphenyl)piperazine (prepared from the commercially available dihydrochloride salt) in 150 ml. of chlorobenzene is refluxed for 5 hours and then cooled. The reaction mixture is washed with two 25 ml. portions of water. The organic layer is dried over anhydrous potassium carbonate and magnesium sulfate and the solvent is stripped with a water pump. The residual amber oil is crystallized by slurrying in isopropanol. Recrystallization from 150 ml. of propanol (using charcoal for decolorization) gives the desired product as a white solid, m.p. 155°-157° C.

EXAMPLE 7

$N^2$-(2-Diethylaminoethyl)-$N^2$-ethyl-$N^4$,$N^6$-bis(1,1,2,2-tetramethylpropyl)melamine dihydrochloride A mixture of 10.5 g. of 2-chloro-4,6-bis[(1,1,2,2-tetramethylpropyl)amino]-s-triazine and 29 g. of 1-ethylamino-2-diethylaminoethane is heated at reflux for 2 hours and poured into water. The resulting gummy oil is washed twice by decantation, extracted into ether, dried over magnesium sulfate, filtered and treated with excess hydrogen chloride gas. The precipitate is collected, washed with ether, dried, dissolved in a minimum of hot isopropanol, treated with charcoal, filtered and cooled. The precipitate is washed with ether, dried, and then heated to 85° C. in 400 ml. of dioxane, filtering while hot. Cooling produces the desired product as colorless crystals, m.p. 246°-248° C.

EXAMPLE 8

4-{4,6-Bis[1,1,2,2-tetramethylpropyl)amino]-s-triazin-2-yl}-1-piperazinecarboxylic acid ethyl ester A mixture of 6.84 g. of 2-chloro-4,6-bis[(1,1,2,2-tetramethylpropyl)amino]-s-triazine and 6.32 g. of N-carbethoxypiperazine in 100 ml. of chlorobenzene is refluxed for 17 hours and then cooled. The reaction mixture is washed with two 25 ml. portions of water, dried over potassium carbonate and magnesium sulfate and stripped of solvent with a water pump. The residual oil is crystallized from 150 ml. of 2B ethanol, treated with charcoal and filtered through celite. The filtrate is cooled to −10° C., filtered and the solid is collected and dried at 78° C., in vacuo over phosphorus pentoxide giving the desired product, mp. 142°-144° C.

EXAMPLE 9

$N^2$-Methyl-$N^2$-[2-(2-pyridyl)ethyl]-$N^4$,$N^6$-(1,1,2,2-tetramethylpropyl)melamine A mixture of 6.84 g of 2-chloro-4,6-bis[(1,1,2,2-tetramethylpropyl)amino]-s-triazine and 27 g. of 1-methylamino-2-(2-pyridyl)ethane is stirred overnight at room temperature and then poured into water yielding a yellow gum. This gum is washed with water, dried and dissolved in 75-100 ml. of acetonitrile. The solution is treated with charcoal, filtered and cooled producing colorless crystals, melting at 109°-110° C. Additional product may be obtained from the acetonitrile mother liquor by the addition of water.

EXAMPLE 10

$N^2$-(2-Dimethylaminoethyl)-$N^2$-methyl-$N^4$,$N^6$-bis(1,1,2,2-tetramethylpropyl)melamine dihydrochloride A mixture of 10.5 g. of 2-chloro-4,6-bis[(1,1,2,2-tetramethylpropyl)amino]-s-triazine and 30.6 g. of 1-methylamino-2-dimethylaminoethane is refluxed for 6 hours, cooled and poured into water yielding a cream colored gum. The gum is washed with water, dried, then dissolved in 15 ml. of boiling acetonitrile and filtered. The filtrate is treated with charcoal, filtered, cooled and stripped to dryness giving a yellow oil. This oil is dissolved in 200 ml. of ether, filtered and treated with hydrogen chloride gas giving a colorless precipitate which is collected, washed with ether and dried. This solid is dissolved in 100 ml. of isopropanol, filtered and precipitated with 800 ml. of ether. The white solid is collected, dissolved in 100 ml. of chloroform, treated with charcoal and precipitated with 400 ml. of ether giving the desired product as colorless crystals, m.p. 267°-270° C.

EXAMPLE 11

$N^2$-(2-Dimethylamino-1-methylethyl)-$N^4$,$N^6$-bis(1,1,2,2-tetramethylpropyl)melamine dihydrochloride A 10.5 g. portion of 2-chloro-4,6-bis[(1,1,2,2-tetramethylpropyl)amino]-s-triazine and 20.2 g. of 1-dimethylamino-2-aminopropane are combined and heated with stirring for one hour. The mixture is filtered hot through celite and treated with excess water giving a gum which solidifies. The solid is collected, washed with water, dried, dissolved in ether, dried over magnesium sulfate and treated with hydrogen chloride gas giving a colorless solid. This solid is washed with ether, dried, dissolved in 100 ml. of hot isopropanol, treated with charcoal, filtered and cooled. The crystals are removed and dried, and melt at 267°–270° C. (dec.). Additional product may be obtained from the mother liquor by the addition of ether.

EXAMPLE 12

2-(1-Piperazinyl)-4,6-bis[(1,1,2,2-tetramethylpropyl)amino]-s-triazine

A 21 g. portion of piperazine in 500 ml. of methyl cellosolve is treated with 17.1 g. of 2-chloro-4,6-bis[(1,1,2,2-tetramethylpropyl)amino]-s-triazine. The mixture is stirred at reflux for 8 hours and then at room temperature. The mixture is filtered and the filtrate is taken to dryness in vacuo. The residue is shaken with 200 ml. of water, filtered, the insolubles collected, washed with 500 ml. of water and dried. The solid is suspended in 500 ml. of boiling ethanol, 150 ml. of methyl cellosolve is added and the mixture is concentrated to 300 ml., clarified and cooled to 10° C. The mixture is then taken to dryness in vacuo and the residue is recrystallized from 250 ml. of 60% ethanol with charcoal. The solid is washed with 100 ml. of 50% cold ethanol and dried giving the desired product, m.p. 183°–185° C.

EXAMPLE 13

Preparation of 50 mg. Tablets

| Per Tablet | | Per 10,000 Tablets |
|---|---|---|
| 0.050 gm. | 2-(3-diethylaminopropyl-amino)-4,6-bis(1,1,2,2-tetramethylbutylamino)-s-triazine | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 2-(3-diethylaminopropylamino)-4,6-bis)1,1,2,2-tetramethylbutylamino)-s-triazine, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 14

Preparation of Oral Suspension

| Ingredient | Amount |
|---|---|
| 2-(3-piperidinopropylamino)-4,6-bis(1,1,3,3-tetramethylbutylamino)-s-triazine | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water gs. ad. | 100 ml. |

The sorbitol solution is added to 40 ml. of distilled water and the 2-(3-piperidinopropylamino)-4,6-bis(1,1,3,3-tetramethylbutylamino)-s-triazine is suspended therein. The saccharin, sodium benzoate, flavor and dye are added and dissolved. The volume is adjusted to 100 ml. with distilled water. Each ml. of syrup contains 5 mg. of 2-(2-adamantylamino)-4,6-bis(1,1,3,3-tetramethylbutylamino)s-triazine.

EXAMPLE 15

Preparation of Parenteral Solution

In a solution of 700 ml. of propylene glycol and 200 ml. of water for injection is suspended 20.0 grams of $N^2$-(2-dimethylamino-2-methylethyl)-$N^2$-isopropyl-$N^4,N^6$-bis(1,1,2,2-tetramethylpropyl)melamine with stirring. After suspension is complete the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 16

Preparation of Topical Cream

| Ingredient | Amount |
|---|---|
| 2-(4-methyl-1-piperazinyl)-4,6-bis(1,1,2,2-tetramethylbutylamino)-s-triazine | 1.0% |
| Ethoxylated stearyl alcohol | 10.0% |
| Benzyl alcohol | 0.9% |
| Isopropyl palmitate | 5.0% |
| Glycerin | 5.0% |
| Sorbitol solution (USP) | 5.0% |
| Lactic acid gs to pH 4.0–5.0 | |
| Water gs ad | 100.00% |

The ethoxylated stearyl alcohol and isopropyl palmitate are heated to liquifying temperature. About 95% of the total volume of water is placed in a separate container followed by the glycerin and sorbitol solution. This aqueous mixture is brought to a boil and then cooled to 60°–75° C. The 2-(4-methyl-1-piperazinyl)-4,6-bis(1,1,2,2-tetramethylbutylamino)-s-triazine adjusted to 4.0–5.0 with lactic acid. The batch is cooled with minimum agitation until the cream sets in its final form.

EXAMPLE 17

Preparation of Intra-articular Product

| Ingredient | Amount |
|---|---|
| 2-(4-phenyl-1-piperazinyl)-4,6-bis(1,1,3,3-tetramethylbutylamino)-s-triazine | 2-20 mg. |
| NaCl (physiological saline) | 0.9% |
| Benzyl alcohol N.F. | 0.9% |
| Sodium carboxymethylcellulose | 1.5% |
| pH adjusted to 5.0-7.5 | |
| Water for injection qs ad | 100% |

EXAMPLE 18

Preparation of Injectable Depo Suspension

| Ingredient | % W/V |
|---|---|
| $N^2$-(2-pyrrolidinoethyl)-$N^4,N^6$-bis(1,1,2,2-tetramethylbuty)melamine | 0.05-5 |
| Polysorbate 80 USP | 0.2 |
| Polyethylene glycol 4000 USP | 3.0 |
| Sodium Chloride USP | 0.8 |
| Benzylalcohol N.F | 0.9 |

-continued

| Preparation of Injectable Depo Suspension | |
|---|---|
| Ingredient | % W/V |
| HCL to pH 6-8 | qs |
| Water for injection qs ad | 100.0 |

EXAMPLE 19

Preparation of N²,N³,N⁶-tris(tert.-butyl)melamine

Cyanuric chloride (9.22 g) was dissolved with heating in toluene (50 ml.) in a glass tube and then cooled to room temperature. t-Butylamine (32.9 g, 47.3 ml.) was then added dropwise with mixing over ½ with cooling to modify the exothermic reaction that results. The tube was then placed in a bomb and the bomb heated in an oil bath maintained at 190°-210° for 20 hours. After cooling the bomb was dismantled, and the contents of the glass tube and the bomb were rinsed into a round bottom flask with water and chloroform. Aqueous sodium hydroxide (10 N, 50 ml.) was added and the solvent was removed in vacuo. The contents of the flask were dissolved in chloroform and water and the chloroform layer separated. The aqueous solution was extracted two times with chloroform, the combined chloroform extracts washed three times with water, dried over anhydrous magnesium sulfate. After filtered through magnesol and washing the magnesol with chloroform removal of solvents gave a white crystalline compound which was recrystallized from chloroform/n-heptane giving white crystals m.p. 185° C.

We claim:

1. The method of inhibiting the progression of arthritis in a mammal which comprises administering to said mammal an effective amount of a compound selected from the group consisting of those of the formula:

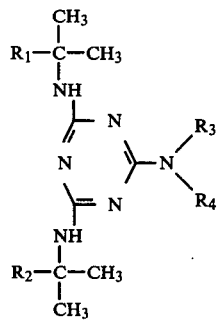

wherein $R_1$ and $R_2$ are each individually selected from the group consisting of methyl, tert.-butyl, tert.-amyl, neopentyl and 3,3-dimethylbutyl; $R_3$ is hydrogen or alkyl having up to 4 carbon atoms; $R_4$ is selected from the group consisting of tert.-butyl, 1,1,2,2-tetramethylpropyl, 1,1,2,2-tetramethylbutyl, 1,1,3,3-tetramethylbutyl, 1,1,4,4-tetramethylamyl, 2-(2-pyridyl)-ethyl and a moiety of the formula:

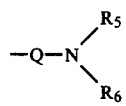

wherein Q is a moiety of the formulae:

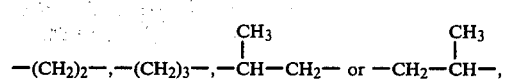

$R_5$ and $R_6$ are each alkyl having up to 4 carbon atoms and $R_5$ and $R_6$ taken together with their associated Nitrogen is pyrrolidino, piperidino, morpholino or thiomorpholine; and $R_3$ and $R_4$ taken together with their associated Nitrogen is selected from the group consisting of pyrrolidino, piperidino, hexamethyleneimino, heptamethyleneimino and a moiety of the formula:

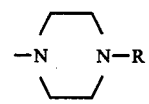

wherein R is hydrogen, alkyl having up to 4 carbon atoms, phenyl, p-methoxyphenyl or carboalkoxy having up to 4 carbon atoms; and the non-toxic acid-addition and quaternary ammonium salts thereof.

2. The method of inhibiting progressive joint deterioration in a mammal which comprising administering to said mammal in effective amount of a compound selected from the group consiting of those of the formula:

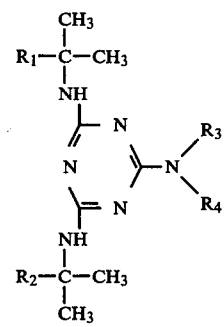

wherein $R_1$ and $R_2$ are each individually selected from the group consisting of methyl, tert.-butyl, tert.-amyl, neopentyl and 3,3-dimethylbutyl; $R_3$ is hydrogen or alkyl having up to 4 carbon atoms; $R_4$ is selected from the group consisting of tert.-butyl, 1,1,2,2-tetramethylpropyl, 1,1,2,2-tetramethylbutyl, 1,1,3,3-tetramethylbutyl, 1,1,4,4-tetramethylamyl, 2-(2-pyridyl)-ethyl and a moiety of the formula:

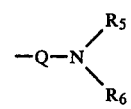

wherein Q is a moiety of the formulae:

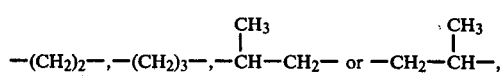

$R_5$ and $R_6$ are each alkyl having up to 4 carbon atoms and $R_5$ and $R_6$ taken together with their associated N(itrogen) is pyrrolidino, piperidino, morpholino or thiomorpholino; and $R_3$ and $R_4$ taken together with their associated N(itrogen) is selected from the group consisting of pyrrolidino, piperidino, hexamethyleneimino, heptamethyleneimino and a moiety of the formula:

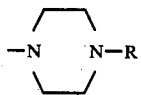

wherein R is hydrogen, alkyl having up to 4 carbon atoms, phenyl, p-methoxyphenyl or carboalkoxy having up to 4 carbon atoms; and the non-toxic acid-addition and quaternary ammonium salts thereof.

3. The method of meliorating inflammation in a mammal which comprises administering to said mammal an effective amount of a compound selected from the group consisting of those of the formula:

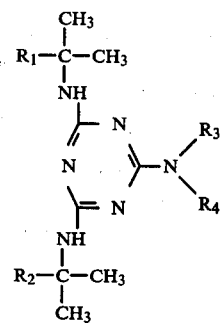

wherein $R_1$ and $R_2$ are each individually selected from the group consisting of methyl, tert.-butyl, tert.-amyl neopentyl and 3,3-dimethylbutyl; $R_3$ is hydrogen or alkyl having up to 4 carbon atoms; $R_4$ is selected from the group consisting of tert.-butyl, 1,1,2,2-tetramethylpropyl, 1,1,2,2-tetramethylbutyl, 1,1,3,3-tetramethylbutyl, 1,1,4,4-tetramethylamyl, 2-(2-pyridyl)-ethyl and a moiety of the formula:

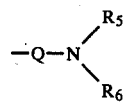

wherein Q is a moiety of the formulae:

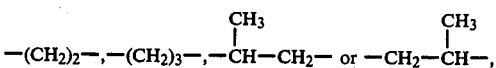

$R_5$ and $R_6$ are each alkyl having up to 4 carbon atoms and $R_5$ and $R_6$ taken together with their associated N(itrogen) is pyrrolidino, piperidino, morpholino or thiomorpholino; and $R_3$ and $R_4$ taken together with their associated N(itrogen) is selected from the group consisting of pyrrolidino, piperidino, hexamethyleneimino, heptamethyleneimino and a moiety of the formula:

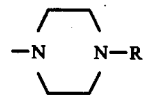

wherein R is hydrogen, alkyl having up to 4 carbon atoms, phenyl, p-methoxyphenyl or carboalkoxy having up to 4 carbon atoms; and the non-toxic acid-addition and quaternary ammonium salts thereof.

* * * * *